United States Patent [19]

Lee et al.

[11] Patent Number: 4,496,249

[45] Date of Patent: Jan. 29, 1985

[54] METHOD AND APPARATUS FOR DETERMINING RELATIVE SURFACE AREAS OF A COATED MATERIAL ON A SUBSTRATE

[75] Inventors: Hong H. Lee, Gainesville, Fla.; Dennis J. Miller, Haslett, Mich.

[73] Assignee: University of Florida, Gainesville, Fla.

[21] Appl. No.: 421,905

[22] Filed: Sep. 23, 1982

[51] Int. Cl.³ .................... G01K 17/06; G01K 25/22
[52] U.S. Cl. .................................. 374/7; 73/204; 422/88; 436/37
[58] Field of Search ................. 374/31, 7, 45, 44; 422/69, 78, 88, 90; 436/5, 37

[56] References Cited

U.S. PATENT DOCUMENTS

| | | | |
|---|---|---|---|
| 3,124,952 | 3/1964 | Johnson | 73/23.1 |
| 3,149,941 | 9/1964 | Barnitz et al. | 73/23.1 X |
| 3,467,501 | 9/1969 | Groszek | 436/37 |
| 3,567,388 | 3/1971 | Kapff | 436/37 X |
| 3,598,534 | 8/1971 | Templer | 374/31 X |
| 3,841,155 | 10/1974 | Koehler et al. | 374/33 X |
| 3,972,681 | 8/1976 | Clack et al. | 374/31 X |
| 4,246,228 | 1/1981 | Jones et al. | 422/88 X |

OTHER PUBLICATIONS

"Automatic Apparatus for Catalyst Characterization by Temp.-Programmed Reduction/Desorption/Oxidation", Boer et al., pp. 349–361 of Rev. Sci. Instrum. 53, Mar. '82.

*Primary Examiner*—Daniel M. Yasich
*Attorney, Agent, or Firm*—Arthur G. Yeager

[57] ABSTRACT

A method of determining the proportion of the surface area of a coated substrate that is covered by the coating comprising passing a known volume of an adsorbate gas under controlled flow conditions over a coated substrate and measuring the volume of adsorbate gas adsorbed on the surface area at different temperatures between the liquefaction temperature of the adsorbate gas and ambient temperature; similarly measuring the volume of the adsorbate gas adsorbed on the surface area of the substrate in the absence of the coating in the same temperature range; similarly measuring the volume of the adsorbate gas adsorbed on said coating in the absence of said substrate in the same temperature range; comparing the above volumes at identical temperatures and calculating therefrom the proportion of surface area of said substrate covered by said coating; and an apparatus for practicing said method. This method in this apparatus is especially useful in measuring the surface area of catalytic material on a supported catalyst.

10 Claims, 8 Drawing Figures

METHOD AND APPARATUS FOR DETERMINING RELATIVE SURFACE AREAS OF A COATED MATERIAL ON A SUBSTRATE

BACKGROUND OF THE INVENTION

The exposed catalyst surface area of a supported catalyst is perhaps the most pursued quantity in the area of catalytic research. Dispersion and specific activity derivable from this measurement are essential for characterization of catalytic reactions. This measurement also gives a measure of the efficiency of dispersion of a supported catalyst. Several methods are available for the measurement, such as electron microscopy, X-ray techniques including diffraction and scattering, and gas chemisorption. (as described by R. J. Farrauto in *A.I.Ch.E. Symposium Series*, 70 (143),9,1974). Of these methods, the gas chemisorption method is perhaps the most accurate and certainly the easiest to implement. Chemisorption has been successful in a number of systems; e.g. $H_2$ on Pt, $H_2$ on Ni, CO on Pd, and NO on oxides of Cu, Ni, and Fe. However, several difficulties limit the utility of chemisorption in determining active surface area, the most important being the question of stoichiometry between surface atoms and adsorbed gas. In addition, only a fraction of the exposed surface is covered by chemisorbed gas molecules for some catalysts, which is usually true for catalysts of metal compounds such as oxides or carbonates. These uncertainties along with the difficulties involving the interactions of gas with catalyst in specific systems have prevented the development of a universal method for active surface area measurement using chemisorption.

Physisorption is the physical adsorption of a gas where there are no chemical attraction forces involved in the adsorption. The physisorption of a gas near its liquefaction point has long been used for the determination of total surface area of a solid. In catalysis, it has been used to determine total support area and pore structure. Because of the nonspecific attractive forces of the typical physisorbed gases, such as nitrogen, physisorption historically contributed little to the determination of the catalyst area. A combination of physisorption and chemisorption has been used by Emmett and Brunauer, J.Am. Chem. Soc., 62, 1732(1940), for the determination of the areas of promoters in iron catalysts.

The very specific nature of interactions between surface atoms and chemisorbed gas, which allows determination of the active surface area, is itself the limiting factor for the application of the chemisorption method to catalysts of metal compounds and metals of unknown stoichiometry. The nondiscriminatory nature of physisorption, on the other hand, makes it unsuitable for the active surface area measurement, yet it offers the advantage that the whole surface is covered by gas molecules regardless of the type of surface involved. It has been found that a universal method based on physisorption can be made applicable to any surface for the determination of catalyst surface area provided that two requirements are met. These requirements are: (1) monolayer coverage of catalyst surface by gas molecules, (2) a means by which the physisorption process can be made selective and specific. The first requirement is not difficult to meet since a proper selection of pressure for given adsorbate and temperature ensures monolayer coverage as the well known BET equation (Brunauer, Emmett, and Teller," Adsorption of Gases in Multimolecular Layers", J. Amer. Chem. Soc. 60, 309., 1938) amply demonstrates. The only requirement here is that the catalyst surface be covered by monolayer of gas molecules and not that the coverage be unity. The very fact that the major interaction in multilayer physisorption is between the first layer of gas molecules and surface atoms (or molecules) ensures monolayer coverage at least at a coverage less than unity. The second requirement is much more difficult to meet. Nevertheless, transient desorption behavior, if not steady state, can exhibit some discriminating features provided that the activation energy for desorption is greater than about 3 kcal/mol, preferably 3-7 kcal/mol. If unique but different characteristics of desorption behavior can be found for catalyst and support, these can be utilized for the determination of the fraction of total surface area occupied by the catalyst.

It is, therefore, an object of this invention to provide a novel method and apparatus for measuring the proportion of surface area of a coated substrate that is covered by the coating, more specifically the proportion of the surface area of a supported catalyst that is covered by the catalytic material. It is another object of this invention to provide such a method and apparatus employing physisorbed gas as the medium for measurement of surface area. Other objects will become apparent from the more detailed description of this invention which follows.

BRIEF DESCRIPTION OF THE INVENTION

This invention provides a method of determining the proportion of the surface area of a solid support that is covered by a catalytic material which comprises passing a known volume of an adsorbate gas, under controlled steady-state conditions of pressure, temperature and flow rate over catalyst material deposited on a solid support maintained at a selected low temperature near the liquefaction temperature of said adsorbate gas and determining the desorption kinetics of the adsorbate gas adsorbed on said catalyst and said support by heating said catalyst material and support from near said liquefaction temperature to ambient temperature and continuously measuring the volume of adsorbate gas desorbed from said catalyst material and support so as to generate data representing the volume of adsorbate gas adsorbed as a function of temperature in a similar fashion determining the desorption kinetics of said adsorbate gas adsorbed on said catalyst in the absence of said solid support at the same range of temperatures; in a similar fashion determining the desorption kinetics of said adsorbate gas adsorbed on said solid support in the absence of said catalyst at the same range of temperatures; comparing the above-determined desorption kinetics of adsorbate gas over identical temperature ranges and calculating therefrom the proportion of surface area of said catalyst material deposited on a solid support that is covered by said catalyst material.

This invention also provides an apparatus for the determination of the surface area of a solid support that is covered by a catalyst material which comprises a thermal conductivity cell having a first and a second subcell for separately measuring thermal conductivities of gases passing therethrough; a mixing tank connected to the inlet of said first subcell, means for introducing into said mixing tank a controlled proportion of a carrier gas and an adsorbate gas at a selected flow rate, a sample cell for receiving gas from said first subcell and immediately passing it into contact with the surface of a solid in said sample cell and thereafter immediately conducting the gas to said second subcell; means to maintain said solid at a selected temperature, and means to measure the flow rate of said gas passing through said second subcell.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawing in which:

DETAILED DESCRIPTION OF THE INVENTION

Figure 1:
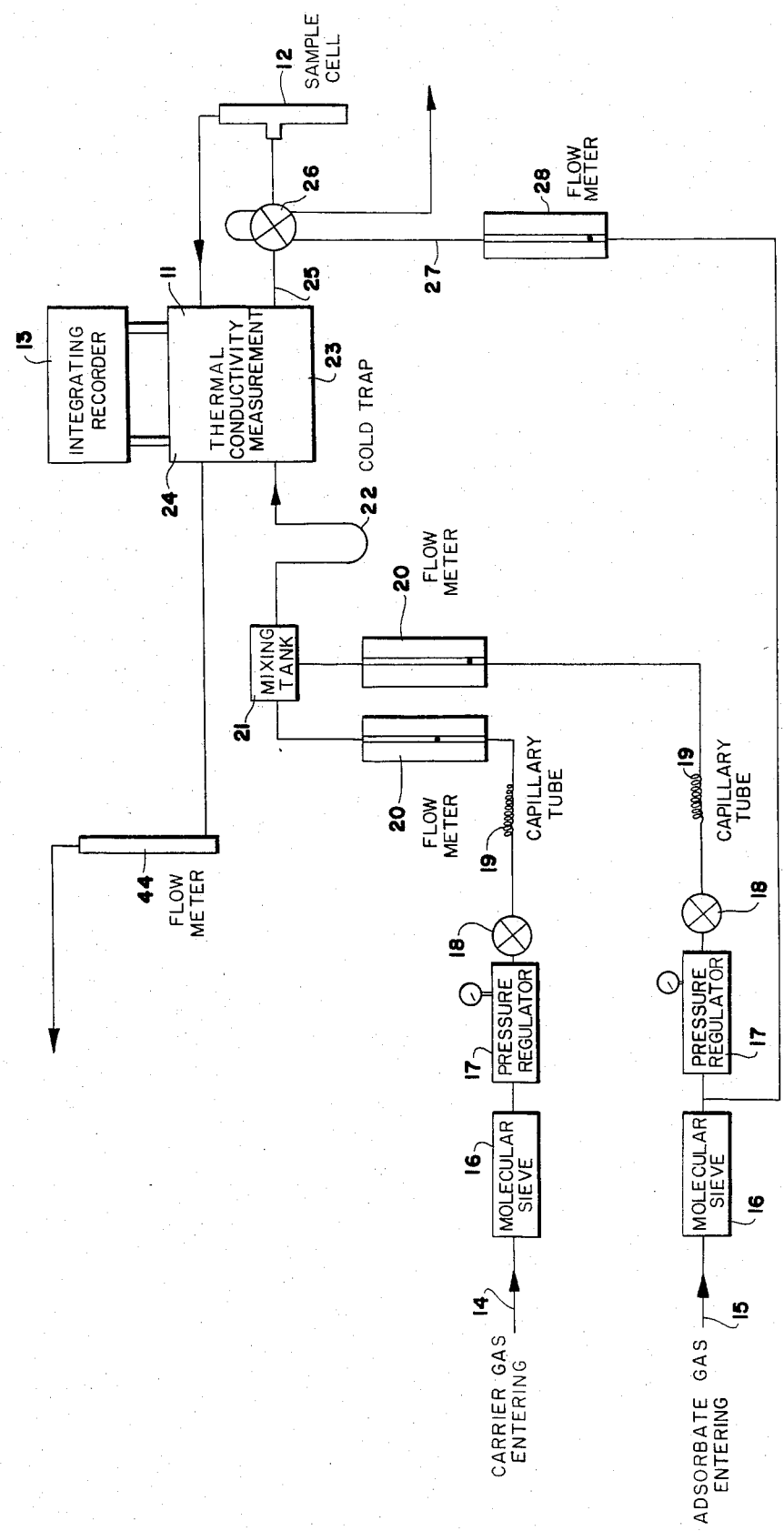
FIG. 1 is a schematic illustration of the apparatus of this invention.

The apparatus of this invention is shown in FIG. 1 and is a continuous flow sorptometer designed for thermal desorption studies and measurements. The principal features of the apparatus are the thermal conductivity cell 11 and the sample cell 12. Thermal conductivity cell 11 is a four-element cell (commercially available) which is connected to an integrating recorder 13 (1.0 mV full scale) which permits measuring differences in composition as low as 200 ppm by volume.

A carrier gas, e.g. helium (Airco, Grade 5, 99.999% pure), is introduced into the apparatus at 14. Other carrier gases that are suitable include neon, argon, krypton, or any other inert gas. The adsorbate gas (i.e. the gas to be adsorbed and desorbed from the surfaces to be measured) may be any of several which do not react with the material of the coating or the substrate, and which have a thermal conductivity substantially different from that of the carrier gas so as to allow easy detection of the difference in cell 11. Among the preferred adsorbate gases are nitrogen (Airco, Grade 5, 99.999% pure) and carbon dioxide (Airco, Grade 4, 99.99% pure). Adsorbate gas is introduced into the apparatus at 15. In each instance, i.e. lines 14 and 15, the respective gas passes through a molecular sieve drier 16, a pressure regulator 17, a shut-off valve 18, a capillary tube section 19, and a flow rate measuring device 20, before both gases are joined together in mixing tank 21.

The molecular sieve drier 16 preferably has an effective pore diameter of 4 angstroms and is capable of removing low concentrations of impurities. The pressure regulator 17 is designed for low pressures, e.g. 0–2 psig and is employed to regulate the flow rate in the range of 0–40 ml/min. Shut-off valves 18 are used to close the line when not in use. Capillary tube section 19 is a length of small diameter tubing employed to dampen any flow irregularities. In a laboratory apparatus this section may be tubing of 0.020 inch diameter having a length of at least about six feet. Flow rate measuring devices 20 may be any reliable apparatus for measuring low flow rates of gases. A preferred apparatus is a rotameter.

Before entering thermal conductivity cell 11 the two gases, carrier gas and adsorbate gas are mixed in tank 21 which may be of any design that will ensure intimate mixing, e.g. internal packing, tortuous tubular paths, internal agitation, etc. The mixed gases leaving tank 21, are preferably conducted through a cold trap 22 for removing any condensibles.

Thermal conductivity cell 11 is divided into two subcells 23 and 24. First subcell 23 measures the thermal conductivity of the gas leaving cold trap 22 and entering cell 11. Second subcell 24 measures that same gas after it passes through sample cell 12. Thus cell 11 is capable of measuring the difference in thermal conductivity of the gas before and after the changes which occur in passage through sample cell 12.

Gas leaving subcell 23 through line 25 flows directly into sample cell 12. There is provided through injection valve 26 the capacity of admitting into line 25 adsorbate gas from line 27. When it is necessary to calibrate this apparatus a known volume of adsorbate gas is admitted to line 25 through valve 26 and the thermal conductivity measurement in subcell 24 will reflect that volume. Line 27 is connected to the source of adsorbate gas 15 and includes a flow rate measuring device (preferably a rotameter) 28 to provide precise control of adsorbate flow rate.

Figure 2:
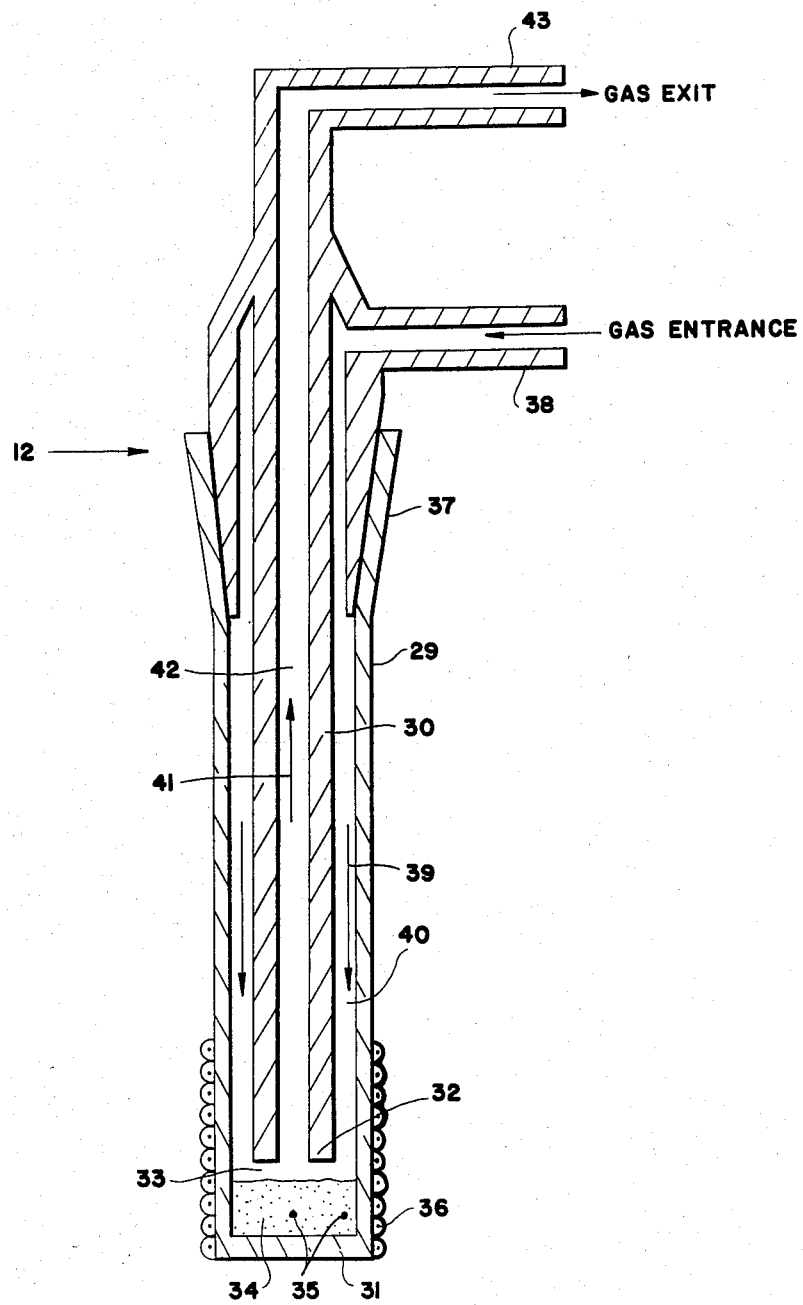
FIG. 2 is a longitudinal cross sectional view of the sample cell of this invention.

Sample cell 12 as seen best in FIG. 2, consists of two concentric tubes, outside tubular portion 29 and inside tubular portion 30. Outside tubular portion 29 is closed and sealed at one end 31 and spaced apart from the adjacent open end 32 of inside tubular portion 30. In this space 33 is placed the sample of coated substrate 34 whose surface area is to be determined in accordance with this invention. Embedded in sample 34 are two micro-thermocouples 35 to monitor the sample temperature and thermal gradients during the measurements. To facilitate heating the sample a heating coil 36 is wrapped around the outside of tubular portion 29 adjacent sealed end 31 which encloses sample 34. Outside tubular portion 29 is sealed to inside tubular portion 30 adjacent the end 37 of outside tubular portion 29. This produces an entrance 38 for gases from first subcell 23 to enter sample cell 12, flow downwardly as shown by arrow 39 in the annulus 40 between outside tubular portion 29 and inside tubular portion 30, pass in contact with the surface of sample 34, flow upward as shown by arrow 41 through the center 42 of inside tubular portion 30 and exit at 43.

Gas leaving exit 43 of sample cell 12 passes through second subcell 24 of thermal conductivity cell 11 where the difference in conductivities is measured in subcells 23 and 24 is noted and plotted on recorder 13. The integral of this signal is representative of the total volume of gas desorbed from sample 34. It can be appreciated that it is important that gas flow rates are well controlled at steady state conditions so that the signal obtained at recorder 13 is truly representative of desorption and does not contain factors due to irregularities in flow rates. The gas exiting from subcell 24 passes through flowmeter 44 and disposed of or recycled for reuse. A soap bubble flowmeter is preferred in laboratory apparatus.

Two types of experiments are performed in the apparatus of this invention; BET surface area measurements and the thermal desorption measurements. The procedure for the BET experiment of Brunauer, Emmett, and Telder is well known and is not discussed here.

The method of this invention involves the measurement of the fractional catalyst surface area of a supported catalyst by determining the differences in desorption kinetics (i.e. adsorption-desorption behavior) of an adsorbate gas on the catalyst material alone and on the support alone.

The adsorption-desorption behavior for the pure components is fully characterized by two pieces of information:

(a) The first is the volume of adsorbate gas adsorbed on one component (catalyst or support) as a function of the temperature of the solid and gas. These data are generated from the thermal desorption experiments, and permit the construction of a curve of volume of adsorbate gas versus temperature.

(b) The second is the monolayer volume of adsorbate gas, as determined from the BET experiment. This monolayer volume is the number of molecules (expressed in volume STP) which are necessary to form a single layer of adsorbed molecules on the component surface. This number is usually expressed as volume per unit weight of sample. Because the molecules adsorb only on the surface, the monolayer volume is an effective measure of surface area.

Figure 5:
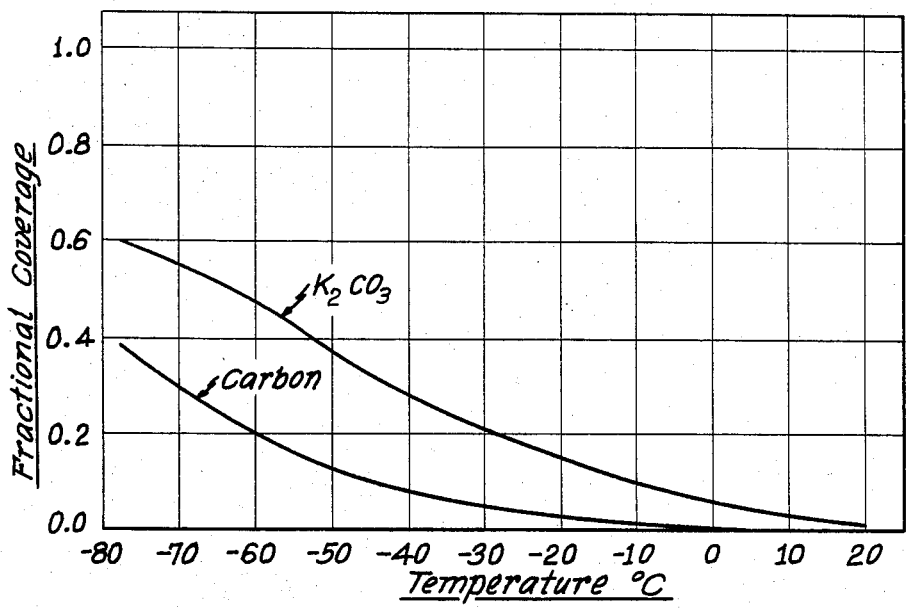
FIG. 5 is a plot of fractional coverage vs. temperature for potassium carbonate and carbon black in Example 1.
Figure 8:
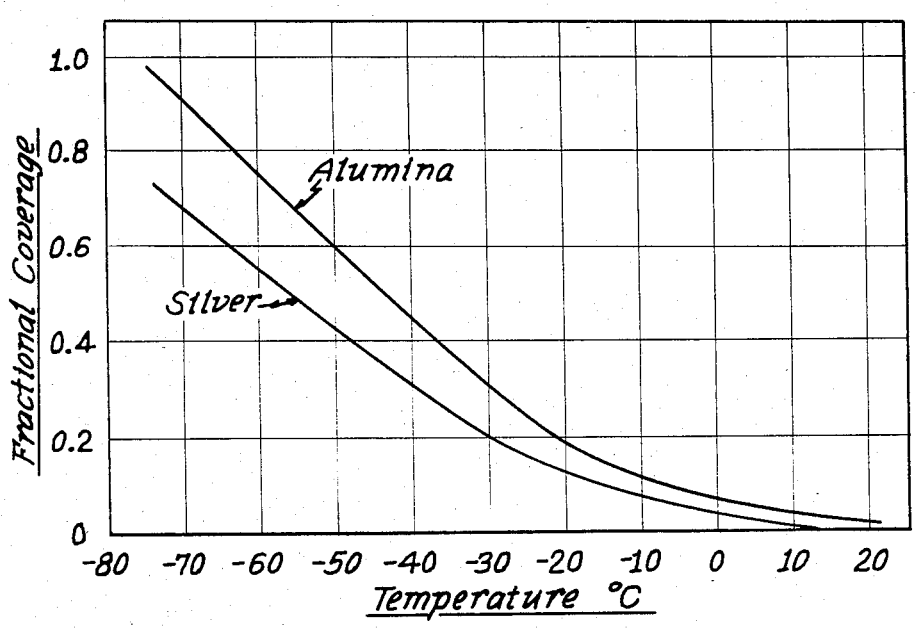
FIG. 8 is a plot of fractional areas vs. temperature for the system of silver-alumina as described in Example 3.

The desorption behavior is characterized by the curve of volume adsorbed versus temperature obtained from thermal desorption, when the volume adsorbed at every point is divided by the monolayer volume from the BET experiment. The resulting curve for the pure component is the fractional coverage (volume adsorbed/monolayer volume) versus termperature, which fully characterizes the desorption behavior. Such curves of fractional coverage, $\theta$, versus temperature, T, as shown in FIGS. 5 and 8.

The desorption behavior for the supported catalyst (catalyst material deposited on a solid support) is characterized by the curve of volume adsorbed versus temperature obtained from the thermal desorption experiments on the supported catalyst. The curve is divided by the total volume adsorbed at the minimum adsorption temperature, (which is near the liquefaction temperature), to give the curve of fraction of volume adsorbed, $\theta$, versus temperature, T. This latter curve describes the desorption behavior for the supported catalyst, such as that shown in FIG. 6.

The fractional catalyst surface area is calculated using the three curves described above; one for each of the pure components and one for the supported catalyst. This is the basic theory for the calculation of fractional surface area. The final result will be Equation (g) given below.

The total volume of adsorbate gas adsorbed on the supported catalyst (two components, 1 & 2, denoting catalyst and support surfaces respectively) is, as a function of temperature $$V_{ads, total}(T) = v_{m1}S_1\theta_1(T) + v_{m2}S_2\theta_2(T) \quad (a)$$

where the units are:

$$V_{ads} = \frac{\text{volume}}{\text{weight}} ; V_m = \frac{\text{monolayer volume}}{\text{area}} ; S = \frac{\text{area}}{\text{weight}} ;$$

$$\theta = \frac{\text{volume adsorbed}}{\text{monolayer volume}}$$

so that $v_{m1}S_1\theta_1$ is the volume adsorbed on component 1 and $v_{m2}S_2\theta_2$ is the volume adsorbed on component 2. The sum of these two is the total volume adsorbed. $S_1$ and $S_2$ are the areas of component one and two on the supported catalyst, so that $S_1 + S_2 = S_t$ (the total catalyst plus support area). $v_{m1}$ and $v_{m2}$ are the monolayer volumes per unit area. For adsorbates other than nitrogen, this monolayer volume per area can be different for different components, so that $v_{m1} \neq v_{m2}$. The quantity $R_i$ is defined as the relative volume ratio:

$$R_i = v_{m1}/v_{m,N2} \quad (b)$$

to normalize the monolayer volume with respect to that for nitrogen. The volume $v_{m,N2}$ is the same for all solid surfaces. The values of $\theta_1(T)$ and $\theta_2(T)$ are taken as the values of fractional coverage (T) for each pure component, so that it is assumed that the surfaces of the supported catalyst and the support are the same as the pure support and pure catalyst.

Equation (a) can be written for any temperature, particularly the minimum adsorption temperature, $T_a$.

$$V_{ads}(T_a) = v_{m1}S_1\theta_1(T_a) + v_{m2}S_2\theta_2(T_a) \quad (c)$$

The fractional volume adsorbed on the supported catalyst (two component solid) is defined as $$\overline{\theta}(T) = V_{ads}(T)/V_{ads}(T_a) = v_{m1}S_1\theta_1(T) + v_{m2}S_2\theta_2(T)/(v_{m1}S_1\theta_1(T_a) + v_{m2}S_2\theta_2(T_a)) \quad (d)$$

Dividing the numerator and denominator by $v_{m,N2}$ introduces the relative volume ratio $R_i$ $$\overline{\theta}(T) = R_1S_1\theta_1(T) + R_2S_2\theta_2(T)/(R_1S_1\theta_1(T_a) + R_2S_2\theta_2(T_a))$$

Now $S_1 + S_2 = S_t$, so that $S_2/S_t = 1 - S_1/S_t$. Dividing by $S_t$ and using $[S_2/S_t = 1 - S_1/S_t]$ to eliminate $S_2/S_t$ from the equation gives $$\theta(T) = R_1\frac{S_1}{S_t}\theta_1(T) + R_2\theta_2(T)\left[1 - \frac{S_1}{S_t}\right] / \left(R_1\frac{S_1}{S_t}\theta_1(T_a) + R_2\theta_2(T_a)\left[1 - \frac{S_1}{S_t}\right]\right) \quad (e)$$

There is only one unknown in this equation, $S_1/S_t$, which is the fractional catalyst surface area. To calculate, the equation is integrated over a temperature range to give the integrals.

$$\int_{T_1}^{T_2} \overline{\theta}(T)dT = \overline{I}$$

$$\int_{T_1}^{T_2} \theta_1(T)dT = I_1$$

-continued $$\int_{T_1}^{T_2} \theta_2(T)dT = I_2$$

Also, $\theta_1(T_a) = \theta_1^a$ and $\theta_2(T_a) = \theta_2^a$
The equation now becomes $$\bar{I} = R_1 \frac{S_1}{S_t} I_1 + R_2 I_2 \left(1 - \frac{S_1}{S_t}\right) / \left(R_1 \frac{S_1}{S_t} \theta_1^a + R_2 \theta_2^a \left(1 - \frac{S_1}{S_t}\right)\right) \quad (f)$$

which can be solved for $S_1/S_t$ to give the equation shown below:

$$\frac{S_1}{S_t} = \frac{R_2 I_2 - R_2 \theta_2^a \bar{I}}{(R_1 \theta_1^a - R_2 \theta_2^a)\bar{I} - R_1 \theta_1^a + R_2 \theta_2^a} \quad (g)$$

where $R_1$ and $R_2$ are calculated from the monolayer volumes of adsorbate and $N_2$ determined from the BET experiments using each gas on the pure components. $\theta_1^a$, $\theta_2^a$, $I_1$, and $I_2$ are all found from the fractional coverage vs. temperature curve determined from the thermal desorption experiments on the pure components. $\bar{I}$ is found from the thermal desorption experiment on the supported catalyst (two component solid). All thermal desorption experiments are carried out at the same partial pressure of adsorbate gas.

In the operation of the above-described method in the apparatus of this invention for thermal desorption, the sample to be analyzed is weighed to the nearest 0.1 mg and placed in the lower part of sample cell 12. The two parts of the cell are joined together and sealed e.g. with stopcock grease at a ground joint. The sample is then degassed in situ by heating the cell and the sample to about 150° C. for 30 minutes.

At the start of a run, the carrier gas and adsorbate gas flows are adjusted to give the desired composition. In the BET runs the composition is changed during the course of the run; in the thermal desorption runs it is essential that the partial pressure of adsorbate gas remains constant throughout the run. While the individual flow rates can be checked initially using the soap bubble flow meter 44, a suitable procedure is to determine those rates at the conclusion of the run experiment, immediately after the thermal desorption runs. After setting the flows approximately using low pressure regulators 17, the apparatus is allowed to stand for 15 minutes to flush all impurities from cold trap 22. Cold trap 22 can be immersed in warm water to aid in the impurities removal, and then is placed in the cooling fluid appropriate for the adsorbate gas used in the run. Power to the conductivity cell is then turned on, and the entire apparatus is allowed to stand for one or two hours until all flow rates have stabilized and a steady baseline is observed on recorder 13. As soon as the baseline has stabilized, the runs can proceed.

With heating wire coil 36 in place and steady state conditions reached, sample cell 12 is immersed to a depth of about one inch into a cooling fluid appropriate for the adsorbate gas. The adsorption process is monitored to give an estimate of the total volume of gas adsorbed, allowing the output signal during desorption to be properly attenuated. The signal from the cell 11 and the temperature are monitored to determine when sample cell 12 has reached a steady state at the selected adsorption temperature.

To initiate thermal desorption, all recorders are turned on simultaneously, the power supply to heating wire 36 is turned on to give the desired heating rate, and the sample cell 12 is immediately removed from the coolant. Sample cell 12 is allowed to heat up to room temperature or above until all gas has desorbed from the sample. Generally a maximum temperature of about 40° C., is sufficient. This adsorption-desorption cycle is preferably repeated several times for each solid sample.

Three additional pieces of information are necessary for the proper analysis of the thermal desorption data. The desorption peak is integrated by the recorder and the result given in arbitrary units. In order to convert these units to a volume of adsorbate, a known volume of adsorbate is injected into the gas stream via sample injection valve 26, and the integral of the recorded peak is used as a calibration to determine the volume of adsorbate in the thermal desorption run. This injection of adsorbate takes place with the sample cell at room temperature, immediately after the thermal desorption runs.

The second piece of information takes into account the fact that cell recorder 13 is actually measuring the gas stream composition downstream from sample cell 12. There is a finite length of tubing between the sample and subcell 24 through which the gas must flow, resulting in a lagging of subcell 24 output behind the temperature outputs. To measure this lag time, sealed end 31 of sample cell 12 can be immersed in the coolant for an instant and then removed. With recorder 13 chart drive on, the time it takes for the small adsorption peak to reach subcell 24 can be recorded and read directly from the chart. The measurement of lag time allows the temperature and volume curves to be brought together for simultaneous calculation.

The third necessary piece of information is the gas phase composition, which is measured by the soap bubble flowmeter. This measurement is always deferred until the thermal desorption runs for all samples in the system being studied have been completed, for it is necessary to shut off one of the gas flows in order to measure the other. Disturbing the gas flow rates is not recommended during the thermal desorption experiments. However, once all experiments have been completed, the total gas flow rate is determined by the soap bubble meter, and then the carrier gas flow is usually determined after the adsorbate flow has been shut off. The adsorbate flow rate, and hence the volume fraction, is determined from the difference of carrier and total flow rate.

The thermal desorption data consists of the two temperature and the TC cell recorder outputs, the calibration peak, and a measurement of the lag time between the sample and the detector. Preferably several thermal desorptions are run for each solid studied, and two are selected to be analyzed. Since the experimental accuracy is related to the instrument stability, those runs which exhibit the most stable baseline should be analyzed individually as described in this section.

Figure 3:
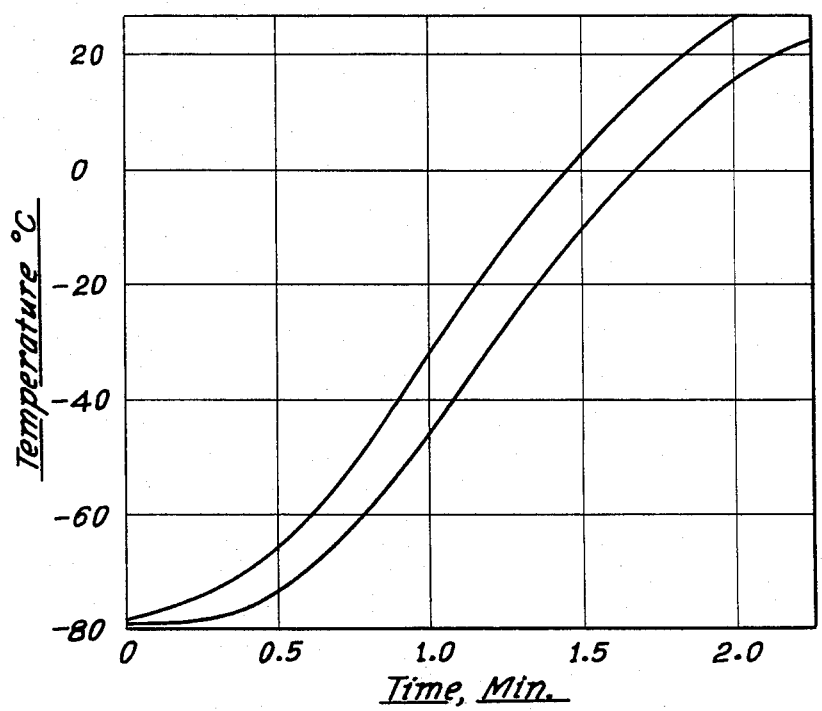
FIG. 3 is a plot of temperature vs. time in the desorption of carbon dioxide from a mixture of silver and carbon black.
Figure 4:
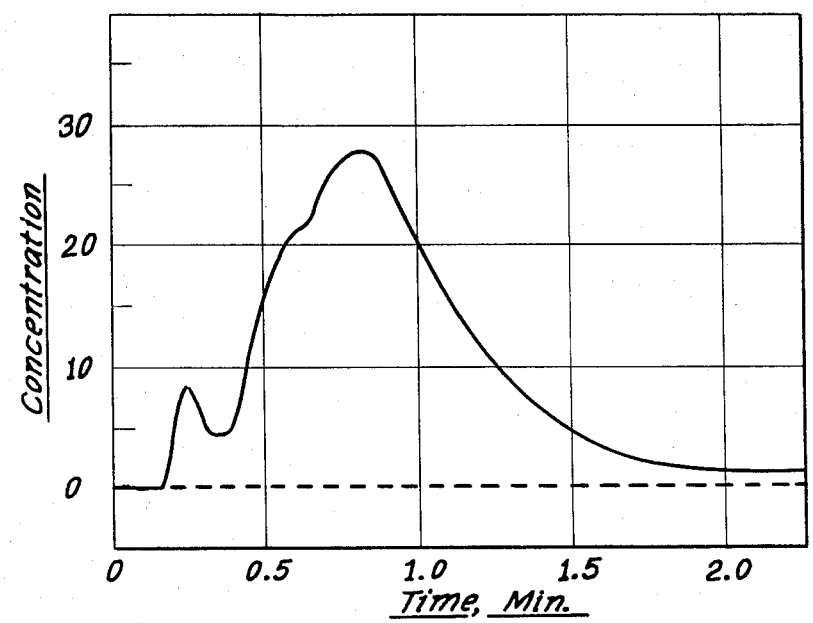
FIG. 4 is a plot of concentration vs. time showing the lag time between the sample cell and the thermal conductivity recorder.

The data from an actual thermal desorption have been reproduced in FIGS. 3 and 4. These data represent the thermal desorption of carbon dioxide from a physical mixture of silver and carbon black. In FIG. 3 there is shown the output of cell 11 and the output of integrator 13 over the run. It can be seen that the baseline has shifted during the desorption. The value of the area under the baseline must be subtracted from the total area under the desorption curve for the entire run, so as to correctly calculate the desorbed volume of gas.

To convert the cell 11 output to a volume desorbed-versus-time-curve, the peak is divided into ten or twelve intervals. In each interval, the area under the desorption curve is found, and the appropriate linear baseline is subtracted to give the net desorption over the time interval. The net desorptions over each interval can be summed over increasing time to yield a curve of extent of desorption versus time. To convert this curve to the volume desorbed, the calibration peak must be used to relate integrator area to the volume of adsorbate gas. Finally, the fraction adsorbed and hence fractional coverage can be calculated by subtracting the desorbed volume curve from the total amount of gas desorbed during the run.

The sample temperature is analyzed by marking the same increments on the temperature charts on the cell 11 output, and then subtracting the value of the lag time from each mark to give a new set of intervals which correspond in the desorption process to the intervals of the cell 11 output. For each of these intervals the temperatures can be determined, and the two temperatures of each interval are averaged to give the average in the cell in each interval. It is now possible to plot the volume adsorbed (or fractional coverage) of adsorbate as a function of solid sample temperature, completing the analysis of the desorption data.

EXAMPLE I

The silver-carbon data of FIG. 3 are analyzed as follows. The conditions under which the experiment was run were 1. total flow rate = 35.0 ml/min.
2. volume fraction $CO_2$ = 0.09
3. chart speeds = 2 in./min.
4. adsorption temperature $T_a$ = −78.9° C.
5. lag time = 0.13 min.

The lag time measurement is not shown or the calibration peak, for which 0.179 ml gave a peak of 408 units, or $4.39 \times 10^{-4}$ ml/unit. The results of cell 11 output analysis are given in Table 1. Column 1 gives the times for which the run is analyzed. Column 2 gives the total area under the desorption curve in the interval $t_i - t_{i-1}$. Column 3 is the linear baseline area to be subtracted. Column 4 gives the actual extent of desorption in the interval. Column 5 gives the sum of the area in all intervals up to $t_i$. Column 6 gives the area converted to volume, in milliliters, using the result from the calibration peak. Column 7 gives the fraction of volume adsorbed at each $t_i$. Columns 8 and 9 give the time intervals to be marked off on the temperature charts and the corresponding average temperature at each $t_i$.

TABLE 1

Calculations for Thermal Desorption

| Pt | 1 Time $t_i$, min | 2 Peak area in interval $(t_i - t_{i-1})$ | 3 Baseline area in interval | 4 Desorbed area in interval | 5 Sum of areas up to $t_i$ | 6 Volume desorbed up to $t_i$, ml | 7 Fraction of volume adsorbed | 8 Time of Temp intervals | 9 T, °C. |
|---|---|---|---|---|---|---|---|---|---|
| 1 | 0.25 | 2.0 | 0 | 2.0 | 2.0 | .0009 | .983 | .12 | 77.7 |
| 2 | 0.5 | 11.7 | 0.2 | 11.5 | 13.5 | .0059 | .886 | .37 | −74.6 |
| 3 | 0.625 | 14.6 | 0.2 | 14.4 | 27.9 | .0122 | .764 | .495 | −70.7 |
| 4 | 0.75 | 18.5 | 0.2 | 18.3 | 46.2 | .0203 | .608 | .62 | −64.9 |
| 5 | 0.875 | 21.0 | 0.3 | 20.7 | 66.9 | .0294 | .432 | .745 | −57.8 |
| 6 | 1.00 | 17.8 | 0.4 | 17.4 | 84.3 | .0370 | .285 | .87 | −49 |
| 7 | 1.25 | 21.8 | 0.9 | 20.9 | 105.2 | .0462 | .107 | 1.12 | −30.2 |
| 8 | 1.5 | 10.2 | 1.1 | 9.1 | 114.3 | .0502 | .030 | 1.37 | −12.6 |
| 9 | 1.75 | 4.5 | 1.3 | 3.2 | 117.5 | .0516 | .003 | 1.62 | +2.7 |
| 10 | 2.0 | 1.9 | 1.5 | 0.4 | 117.9 | .0518 | 0 | 1.87 | 14.5 |

The fraction of volume adsorbed can be plotted as a function of temperature, and analyzed according to the theory for surface area measurement.

The determination of catalyst area by thermal desorption requires information about the individual catalyst and support surfaces, since surface characteristics of the catalyst and support are used to determine the supported catalyst area. The necessary information includes total surface area as measured by nitrogen BET experiment, monolayer volume of carbon dioxide measured by BET, and the thermal desorption fractional coverage versus temperature curves. Also required for the determination are the curves of fractional coverage vs. temperature for the supported catalyst. The information necessary for the two binary systems being considered is summarized in Table 2. In addition, the relative volume ratio R defined as $$R = V_{m,CO_2}/V_{m,N_2} \quad (1)$$

is given in the table. The source of each component is listed in the final column of Table 2.

TABLE 2

Results of BET Experiments for Pure Components

| Component | $V_{m,CO_2} \frac{ml(STP)}{g}$ | $V_{m,N_2} \frac{ml(STP)}{g}$ | S, $\frac{m^2}{g}$ | R | Source |
|---|---|---|---|---|---|
| Carbon Black | 2.62 | 6.14 | 26.8 | .43 | Fisher Scientific |
| Potassium Carbonate | .113 | .183 | 0.80 | .62 | Fisher Scientific |
| Alumina | .069 | .179 | 0.78 | .38 | Norton Co. #SA-5202 |
| Silver | .023 | .048 | 0.21 | .48 | Alfa-Ventron 2.0–3.5μ |

The primary application of the method and apparatus of this invention is area measurement of nonmetallic catalysts where chemisorption or other methods fail. One such nonmetallic catalyst is potassium carbonate, which is an efficient catalyst for steam and hydrogen gasification of coal. Prior to this invention no method has been known for measuring surface area of potassium carbonate supported on carbon. Knowledge of the surface would lead to a better understanding of the catalytic nature of potassium carbonate.

The carbon black used in this example consisted of nonporous particles of diameter 0.1 to 0.2μ, with total surface area as reported in Table 2. The carbon black is graphitized, as evidenced by a hexagonal particle shape under the electron microscope and the hydrophobic nature of the surface.

Potassium carbonate was prepared for surface area measurement by grinding 1 mm crystals overnight in a ball mill grinder purged with nitrogen. The resulting powder was sieved to collect particles less than 0.43 mm (−325 mesh) in diameter, and stored in an inert or vacuum environment to prevent uptake of moisture prior to use in the experiments. Five samples of potassium carbonate impregnated on carbon black were prepared by first dissolving the desired quantity of $K_2CO_3$ in water, and then adding an equal amount of acetone to the solution. The prescribed amount of carbon black was then added to the solution to form a slurry. This slurry was stirred for 15 minutes and then dried for 24 hours under partial vacuum at 90° C. It was found that 2 ml of water per gram of carbon gave a good slurry. The addition of acetone was necessary for the carbon to be wetted. In addition to the slurries for the impregnated samples, potassium carbonate was prepared by crystallization from the acetone-water solution, and pure carbon black was also put through the impregnation procedure in a solution which had no $K_2CO_3$ added. Following preparation, part of each sample was heated in air at 700° C. to oxidize all carbon. The residue was weighted to give the weight percent of potassium carbonate. The pure carbon black contained 0.1% residue. The weight of potassium carbonate for each of the five samples from the pyrolysis is given in Table 3.

TABLE 3

Thermal Desorption Results of $K_2CO_3$ Impregnated Carbon Black

| Sample | Weight % $K_2CO_3$ | $V_{ads}$, $\frac{ml(STP)}{g}$, $CO_2$ | $\theta^a$ | $I_c$, $I_k$, $\bar{I}$ | $\frac{S_k}{S_t}$ |
|---|---|---|---|---|---|
| Carbon Black | 0 | 1.013 | .387 | 8.47 | — |
| 1 | 1.4 | 1.125 | — | 22.3 | .013 |
| 2 | 4.6 | 1.110 | — | 22.3 | .013 |
| 3 | 10.1 | 1.035 | — | 24.2 | .078 |
| 4 | 16.7 | .966 | — | 27.7 | .230 |
| 5 | 26.8 | .885 | — | 25.7 | .138 |
| $K_2CO_3$ | 100 | .0668 | .593 | 21.64 | — |

The thermal desorption runs for the two components and the five impregnated samples were carried out in a single twelve hour period, to assure that the partial pressure was the same for each sample. In addition, a similar weight of sample and experimental procedure was used for all samples to minimize any errors resulting from unforseen effects not predicted by our theory.

Figure 6:
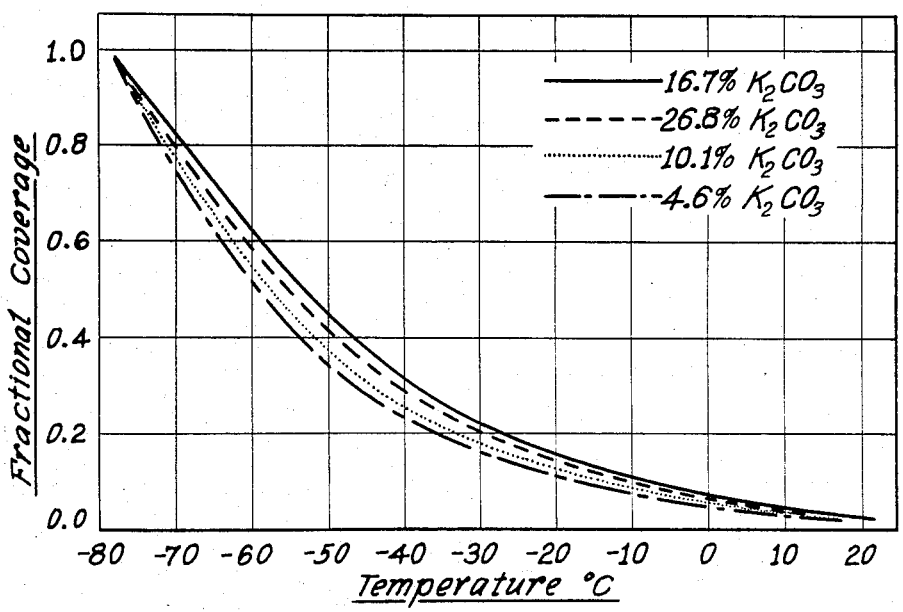
FIG. 6 is a plot of the fraction adsorbed vs. temperature for four impregnated samples described in Example 2.

The raw data from the thermal desorption of carbon dioxide were analyzed as in the sample calculation given earlier. The plots of fractional coverage versus temperature for carbon black and potassium carbonate are shown in FIG. 5 and the graphs of fraction adsorbed versus temperature for four of the impregnated samples are shown in FIG. 6. The curves for the pure components are shown in FIG. 5 are seen to be linearly independent, allowing the fractional surface area of potassium carbonate on each of the impregnated samples to be calculated without determining the total surface are of each sample. The equation used to calculate the fractional area is $$\frac{S_k}{S_t} = \frac{R_c I_c - R_c \theta_c^a \bar{I}}{(R_k \theta_k^a - R_c \theta_c^a)\bar{I} - R_k I_k + R_c I_c}$$

where
$S_k$ = surface area of potassium carbonate in two-component sample
$S_t$ = total surface area of total two component solid
$R_c$ = relative volume ratio of adsorbate on carbon block
$R_k$ = relative volume ratio of adsorbate on potassium carbonate
$I_c$ = integral with respect to carbon black $$= \int_{T_1}^{T_2} \theta_c dt$$

$I_k$ = integral with respect to potassium carbonate $$= \int_{T_1}^{T_2} \theta_k dt$$

$\bar{I}$ = total integral over temperature of fraction desorbed $$= \int_{T_1}^{T_2} \bar{\theta} dt$$

$\theta_c^a$ = fractional coverage of carbon black with adsorbate
$\theta_k^a$ = fractional coverage of potassium carbonate with adsorbate
T = temperature °C.

The integrals $I_c$, $I_k$, and $\bar{I}$ are determined numerically using the trapezoid rule with $\Delta T = 2.5°$ C. over the range −75° C. to 0° C. The values of $\theta_k^a$ and $\theta_c^a$ are determined from the total volume adsorbed on the pure components at the start of the thermal desorption. The data and results for the impregnated samples are given in Table 3.

Several analytical methods were attempted in order to obtain an independent measure of potassium carbonate surface area and thus verify the results obtained by thermal desorption. X-ray studies and transmission and scanning electron microscopy revealed no useful information. X-ray line broadening did not yield useful information. Small angle X-ray scattering produced no useful information. Scanning and transmission electron microscopy similarly yielded no useful information about potassium carbonate area, since it was impossible to distinguish between $K_2CO_3$ and carbon particles when the samples were examined in the microscopes. Thus none of the analytical methods tried gave positive verification of the results obtained by the thermal desorption experiments.

Figure 7:
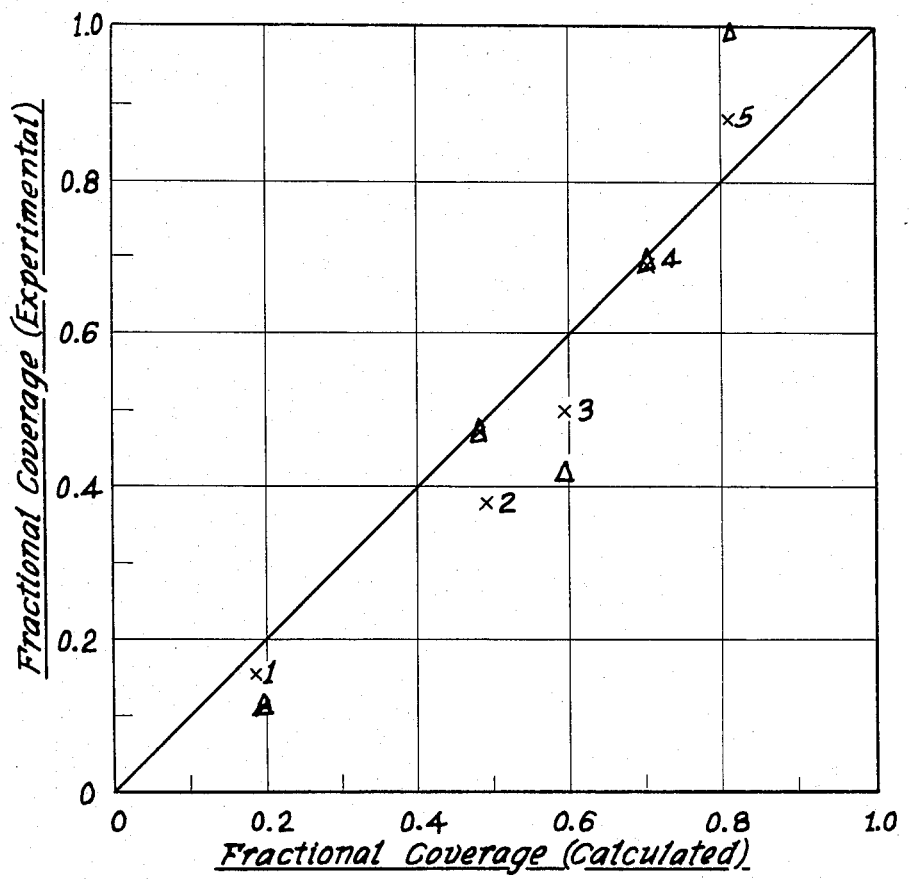
FIG. 7 is a plot of a comparison of experimentally determined values vs. values of fractional areas as described in Example 2.

To obtain partial verification of the method, five samples of physically mixed powders of carbon black and potassium carbonate were prepared by analysis by thermal desorption. Weighed amounts of the two components were placed together and mixed, so that the surface area of each component was known. The $K_2CO_3$ surface area can be calculated from $$\frac{S_K}{S_T} = \frac{\bar{S}_K W_K}{\bar{S}_K W_K + \bar{S}_C (1 - W_k)} \quad (3)$$

where $W_k$ is the weight fraction of $K_2CO_3$ in the physically mixed sample and $\bar{S}_k$ and $\bar{S}_c$ are the total surface areas per gram $K_2CO_3$ and carbon black respectively. The physically mixed samples were analyzed by thermal desorption in the same manner as the impregnated samples. The calculated fractional areas and the fractional areas determined by thermal desorption are given in Table 4. A plot of the experimentally determined areas versus the calculated values if given in FIG. 7.

TABLE 4

Thermal Desorption of Physically Mixed Carbon Black-$K_2CO_3$

| Sample | $W_{K_2CO_3}$ | $(S_k/S_t)_{calc}$ | $\theta^a$ | I, $I_c$, $I_k$ | $(S_k/S_t)_{exp}$ |
|---|---|---|---|---|---|
| Carbon | 0.0 | 0 | .714 | 11.66 | — |
| 1 | 0.888 | .192 | — | 21.6 | .15 |
| 2 | 0.969 | .484 | — | 26.9 | .37 |
| 3 | 0.980 | .589 | — | 28.9 | .49 |
| 4 | 0.987 | .692 | — | 31.5 | .69 |
| 5 | 0.992 | .794 | — | 33.5 | .88 |
| $K_2CO_3$ | 1.0 | 1.0 | 1.189 | 41.0 | — |

To gain a positive verification of the surface area measurement by thermal desorption, a catalyst system was chosen for which the catalyst surface area could be measured by an independent method. For this reason silver catalyst supported on alumina was chosen as a system to be studied, with the expectation of obtaining the silver surface area by oxygen chemisorption or scanning electron microscopy. A further objective is to demonstrate the application of thermal desorption method to metallic as well as nonmetallic catalysts.

Three samples of silver impregnated on alumina were prepared by chemical deposition of silver as described in detail by Forzatti et al. *J. Catalysis* 28, 455 (1973). The loading of silver was varied by exposing one catalyst to single impregnation, the second to double impregnation, and the third to triple impregnation.

The alumina support consisted of fused alumina pellets about 1 cm in diameter, made from 1$\mu$ to 3$\mu$ nonporous alumina spheres bonded to each other by heat and pressure. The pellets were crushed and sieved to retain particles of size 0.074—0.5 mm (−32+200 mesh). These particles are fused aggregates of 1$\mu$ to 3$\mu$ spheres. Attempts to procure pure silver powder by the chemical deposition method were unsuccessful, so a silver powder of 2.0−3.5$\mu$ diameter particles was used as the silver pure component. This silver powder has been reduced along with the impregnated samples to obtain as much similarity between pure and supported silver surfaces as possible.

The nitrogen BET experiments were carried out for the three impregnated samples, so the actual silver surface area could be determined from thermal desorption. These results are given in Table 5. The thermal desorption experiments were carried out for the pure components and the three impregnated samples within an eight hour period, and constant sample weight and similar experimental procedure was used for all samples to assure uniformity of measurement.

TABLE 5

Thermal Desorption of AG—$Al_2O_3$

| Sample | Wt % Ag | $S_T$, m²/g | $V_{m,N2}$ $\frac{ml(STP)}{g}$ | $S_A/S_T$ | $S_A$ |
|---|---|---|---|---|---|
| Ag | — | .21 | .048 | — | — |
| 1 | | 1.04 | .239 | .48 | .50 |
| 2 | | 1.06 | .243 | .52 | .55 |
| 3 | | 1.17 | .268 | .59 | .69 |
| $Al_2O_3$ | | .78 | .179 | — | — |

The thermal desorption experiments for silver and alumina showed that the curves of fractured coverage vs. temperature for the two components were not linearly independent but instead differed only by a multiplicative constant. This restricted the analysis to the use of a more generalized version of the equation in Example 2, using the proper parameters for silver and alumina instead of potassium carbonate and carbon. The silver and alumina curves are given in FIG. 8, and the experimental results of the thermal desorption are given in Table 5 for the three samples studied. The integrals $I_{Al}/\theta_A l^a$, $I_A/\theta_A{}^a$ and $\bar{I}$ for the three samples were identical, thus the calculation of fractional surface area could be carried out by the following simplified formula $$\frac{S_i}{S_t} = \frac{\frac{V_{ads,CO_2}}{V_{m,N2}} - R_{Al}\theta^a_{Al}}{R_A\theta_A{}^a - R_{Al}\theta^a_{Al}}$$

which is obtained by dividing through by the value of $\bar{I}$. This formula requires only the initial conditions of adsorption for calculating fractional area and is useful for estimation in cases where the curves of fractional coverage vs. temperature for the two components are linearly dependent.

To verify the surface area measurements carried out by thermal desorption, the area of silver catalyst was estimated by oxygen pulse chemisorption. Oxygen adsorption on silver is not fully understood: the unknown stoichiometry of the adsorption and the fact that the quantity adsorbed goes through a maximum at 160°-200° C. are two major uncertainties in the process. For this study, the total volume of oxygen chemisorbed was used as a measure of silver surface area, since oxygen is not chemisorbed on alumina. Because of the unknown stoichiometry of the chemisorption, only the relative surface areas of the three samples can be determined by chemisorption.

To carry out the chemisorption, supported silver catalyst was placed in the chemisorption cell and reduced in a stream of flowing hydrogen for twelve hours. An inert gas was then passed through the catalyst to purge all hydrogen prior to the chemisorption step. The pulse chemisorption technique consisted of injecting pulses of oxygen into the inert gas stream which flows over the catalyst. By measuring the volume of the pulse (in a thermal conductivity cell) before and after it passes over the catalyst, the volume of $O_2$ chemisorbed per pulse can be determined. The total amount of $O_2$ adsorbed can be found by adding volume adsorbed from each pulse. Five or six pulses were usually sufficient to saturate the silver surface. Several chemisorption-reduction cycles were carried out for each catalyst studied.

The experimental results from $O_2$ chemisorption are given in Table 6. To facilitate comparison of the results with those of the thermal desorption, the volume adsorbed on Sample 2 from chemisorption was set equal to the fractional area obtained by thermal desorption. This is equivalent to assuming an oxygen fractional coverage of 0.3 on the silver catalyst, if the area of oxygen per molecule is assumed to be the same as nitrogen. The "normalized" values of the fractional surface area determined by chemisorption are shown in the final column of Table 6.

TABLE 6

$O_2$ Chemisorption on $Ag$—$Al_2O_3$

| Sample | Volume $O_2$ Chemisorbed $\frac{ml(STP)}{g}$ | Normalized Silver Area $S_A$, $m^2/g$ | Thermal Desorption Silver Area $S_A$, $m^2/g$ |
|---|---|---|---|
| 1 | .022 | .34 | .50 |
| 2 | .037 | .55 | .55 |
| 3 | .046 | .69 | .69 |

To study the silver surface even further scanning electron microscopy of the three samples was employed. Twelve photographs of each sample were taken at ×48,000, giving about six hundred particles for each sample. The particles were counted and weight-averaged to determine an average particle size. The results obtained are inconclusive for the determination of silver catalyst area. The only information obtained was by visual examination of the pictures, which showed that the area of silver was of the order of 20 to 50% of the total area. The uncertainty in measuring particle diameter is larger than the differences in silver area for the three samples, so that all micrographs appear to be from a single sample and are indistinguishable. This is a general difficulty with the use of miscroscopy for determining supported catalyst surface areas. Factors such as particle shape and catalyst heterogeneities from one position on the surface to another prevent practical use of microscopy for area measurements.

The silver-alumina system studied as described above provided a partial verification of the thermal desorption method. The use of oxygen chemisorption has provided verification of the relative values of catalyst surface area determined by thermal desorption, but lack of information on the oxygen-silver stoichiometry has prevented a comparison of absolute surface areas. Most importantly, however, the success of the thermal desorption method of this system shows applicability in general to metallic catalysts even for cases where the curves of fractional coverage vs. temperature for the two components do not differ greatly. In this respect the silver-alumina experiments must be considered successful.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A method of determining the proportion of the surface area of a solid support that is covered by a catalytic material which comprises passing a known volume of an adsorbate gas under controlled steady-state conditions of pressure, temperature, and flow rate, over a catalyst material deposited on a solid support maintained at a selected low temperature near the liquefaction temperature of said adsorbate gas and determined first the desorption kinetics of the adsorbate gas adsorbed on said catalyst and said support by heating said catalyst material and said support from near said liquefaction temperature to ambient temperature and continuously measuring the volume of adsorbate gas desorbed from said catalyst material and from said support so as to generate data representing the volume of adsorbate gas adsorbed as a function of temperature; in a similar fashion determining secondly the desorption kinetics of said adsorbate gas adsorbed on said catalyst in the absence of said solid support at the same range of temperatures; in a similar fashion determining thirdly the desorption kinetics of said adsorbate gas adsorbed on said solid support in the absence of said catalyst at the same range of temperatures; comparing the above-determined said first, second and third desorption kinetics of adsorbate gas over identical temperature ranges and calculating therefrom the proportion of surface area of said catalyst material deposited on a solid support that is covered by said catalyst material.

2. The method of claim 1 wherein said steps of determining the volume of the adsorbate gas is accomplished by measuring the thermal conductivity of said gas.

3. The method of claim 1 wherein said step of comparing includes a determination of the total surface area of said catalyst material and the uncovered portion of said solid support.

4. An apparatus for determination of the surface area of a solid support that is covered by a catalyst material which comprises a thermal conductivity cell having a first and a second subcell for separately measuring and recording thermal conductivities of gases passing therethrough; a mixing tank connected to the inlet of said first subcell, means for introducing into said mixing tank a controlled proportion of a carrier gas and an adsorbate gas at a selected flow rate, a sample cell for receiving gas from said first subcell and immediately into contact with the surface of a sample of said solid support covered by the catalyst material in said sample cell and thereafter immediately conducting the gas to said second subcell; means to measure the temperature of said sample; means to maintain said sample at a selected temperature, and means to measure the flow rate of said gas passing through said second subcell.

5. The apparatus of claim 4 which includes, between said mixing tank and said first subcell, a cold trap.

6. The apparatus of claim 4 which includes two inlet conduits to said mixing tank, each said conduit including a flow rate measuring device, a shut-off valve, a pressure regulator, and a drier.

7. The apparatus of claim 4 wherein said sample cell includes two concentric tubular partions, the outside tubular portion being closed at one end and sealed to the inner tubular portion at the other open end, said closed end being spaced apart from the adjacent open end of said inner tubular portion, an inlet conduit communicating with said outer tubular portion adjacent said sealed end, an outlet conduit communicating with said inner tubular portion, and thermocouple sensors in said closed end in the space between said outer tubular portion and said inner tubular portion.

8. The apparatus of claim 7 wherein said closed end of said sample cell includes a means for heating said closed end.

9. The apparatus of claim 8 wherein said heating means comprises electric resistance heating wire wrapped around the outside of said outside tubular portion.

10. The apparatus of claim 7 wherein said conduit includes a means for dampening flow irregularities.

* * * * *